(12) United States Patent
Raffer

(10) Patent No.: US 6,499,336 B1
(45) Date of Patent: Dec. 31, 2002

(54) ROTATIONAL RHEOMETER

(75) Inventor: Gerhard Raffer, Graz (AT)

(73) Assignee: Anton Paar GmbH, Graz (AT)

( * ) Notice: Subject to any disclaimer, the term of this patent is extended or adjusted under 35 U.S.C. 154(b) by 0 days.

(21) Appl. No.: 09/669,778

(22) Filed: Sep. 25, 2000

(30) Foreign Application Priority Data

Sep. 24, 1999 (AT) .............................................. 1634/99

(51) Int. Cl.$^7$ .............................................. G01N 11/14
(52) U.S. Cl. .................... 73/54.28; 73/54.23; 73/54.38; 73/54.39
(58) Field of Search .............................. 73/54.23, 54.28, 73/54.29, 54.38, 54.35, 54.37, 54.39

(56) References Cited

U.S. PATENT DOCUMENTS 5,349,847 A * 9/1994 Lee et al. .................. 73/54.28

FOREIGN PATENT DOCUMENTS

SU 670855 * 6/1979 ................. 73/54.39

OTHER PUBLICATIONS van Vliet, T., et al. "A Constant Stress, Parallel Plate Viscometer Without Bearing for Very Low Shear Stresses", J. Phys. E: Sci. Instrum., vol. 14, No. 6, Jun. 181, pp. 745 and 746.*

* cited by examiner

Primary Examiner—Daniel S. Larkin
(74) Attorney, Agent, or Firm—Towsend and Townsend and Crew LLP

(57) ABSTRACT

A rotational rheometer has an integrating motor (1), which rotates a measuring shaft (16) supporting a first measuring element (4), there being formed between this first measuring element (4) and a further, fixed measuring element (5) a measurement gap (S), into which is introduced the substance to be tested (12), in particular fluid, the depth of the measurement gap (S) being variable by the adjustment of the two measuring elements (4, 5) relative to each other, and a device being provided to determine the distance between the two measuring elements. At least one inductive or at least one magnetic position sensor (19, 21) is supported by one of the two measuring elements (4, 5). The first measuring element (4) or a device (18) disposed on this measuring element (4) can cause the position sensor (19, 21) disposed on the other measuring element (5) to respond, or can cause the output signal, e.g. impedance, resistance, or voltage, of this position sensor (19, 21) to be modified, and the output signals of the position sensor (19, 21) are supplied to an analyzing unit (22, 24, 17).

22 Claims, 2 Drawing Sheets

ROTATIONAL RHEOMETER

BACKGROUND OF THE INVENTION

The invention relates to a rotational rheometer.

The basic structure of rotational rheometers is known from Austrian patent 404 192. A rotational rheometer of the type referred to above is known from DE-A-34 23 873. This document describes a rotational rheometer whose rotor is coupled to a test specimen and is suspended in a stator by a low-friction bearing system. A compensation arrangement which compensates for bearing torque on the rotor over the full range of rotation of the rotor is provided. Also provided are position transducers which are able to determine accurately the angular position of the rotor over the full 360° range of rotation. Also provided is a transducer with which the longitudinal position of the rotor relative to the stator can be accurately detected. The disadvantage is that, with this rheometer, thermal expansion, the rigidity of the stand, and temperature drift in the stand affect the measurement process.

SUMMARY OF THE INVENTION

An object of the present invention is to avoid having indirectly to measure the distance between the measuring elements of rotational rheometers having these basic principles, i.e. to avoid having to take the circuitous route of measuring the distance between a point on the measuring shaft and a point on the stand or stator. Instead, the object is to be able directly to measure, and/or set, and/or keep constant the distance between the measuring elements forming the measurement gap S. This is important, since even minor fluctuations in the depth of the measurement gap S in the course of the measurement process, e.g. as a result of fluctuations in temperature, in particular of the stand and/or the measuring elements, have a considerable effect on the accuracy of measurement.

According to the invention, non-contact position sensors are therefore provided, or are supported by one of the two measuring elements bounding the measurement gap S, to establish or measure, and/or set, and/or keep constant the depth of the measurement gap S. The other respective measuring element supports the component which causes the position sensor to respond, or itself causes the position sensor to respond. The output signals of the position sensors are supplied to the analyzing unit; advantageously, the output signals of the analyzing unit, in dependence upon the output signals of the position sensor, control a device for modifying or setting the measurement gap by adjusting the height at least of one of the two measuring elements.

Preferred embodiments of the invention employ different embodiments or variants of position sensors which enable the depth of the measurement gap S to be measured very precisely in a non-contact manner, or which react very sensitively to fluctuations in the distance between the mutually opposite measuring elements.

The accuracy of the position sensors used according to the invention is sufficient to achieve the accuracy required in setting the depth of the measurement gap. The measurement errors hitherto caused by the lack of accuracy in setting the depth of the measurement gap are largely eliminated thereby.

Another aspect of the invention enables measurement errors caused by fluctuations in temperature to be largely eliminated and advantageously enables rapid analysis to take place.

In the analyzing unit, the measurement gap depth values measured with the position sensors are combined with the measurement values for the moment of the substance to be tested and, if need be, with the measurement values of a normal force measurement device; they are then used to calculate viscosity.

In a rotational viscometer where measurements are taken of a specimen or substance with the height h, which is generated by the depth of the measurement gap S between a fixed measuring element (plate) and a measuring element (plate) which rotates relative thereto and has a radius R, the following relationships apply to the shear rate D (1) and viscosity $\eta$ (2):

$$D_{(R)} = \frac{\omega * R}{h} \quad (1)$$

$$\eta = \frac{\tau}{D_{(R)}} = \frac{2*M}{\pi*R^3} * \frac{1}{D_{(R)}} = \frac{2*M*h}{\pi*R^4*\omega} \quad (2)$$

If, for example, a constant torque M is pre-selected, a change in the height h causes the angular velocity $\omega$ to fluctuate in the same proportion, as a result of which the calculated viscosity remains constant. If a height fluctuation is not allowed for in the calculation, however, the following error results for the viscosity $\eta$.

If h'=k*h (error factor k) is used for the height, the result is equation (3) for the true angular velocity:

$$\omega' = \frac{D_{(R)} * h'}{R} \quad (3)$$

and equation (4) for the viscosity established:

$$\eta = \frac{2*M*h}{\pi*R^3*D_{(R)}*h'} = C*\frac{h}{h'} = C*\frac{1}{k} \quad (4)$$

h=calculated specimen height [m]
h'=true specimen height [m]
$D_{(R)}$=shear rate at the radius "R" [1/s]
$\omega$=calculated angular velocity [1/s]
$\omega'$=true angular velocity [1/s]
$\tau$=shear stress [Pa]
M=torque [Nm]
$\eta$=viscosity [Pa·s]

$$C = \frac{2*M}{\pi*R^3*}D_{(R)}$$

It is clear from the above derivation that, if there is a measurement error in the specimen height, viscosity fluctuates in inverse proportion to the height ratio, that is to say, a +1% height measurement error produces a 1% reduction in viscosity. The measurement gap is generally 1 to 2 mm; for a viscosity error of <1%, the size of the gap therefore has to be determined with an accuracy better than 10 $\mu$m or 20 $\mu$m.

Advantageous embodiments of the invention will become clear from the following description, claims, and drawings.

The invention will be described below in detail, by way of example, with reference to the drawings.

DESCRIPTION OF THE PREFERRED EMBODIMENTS

Figure 2:
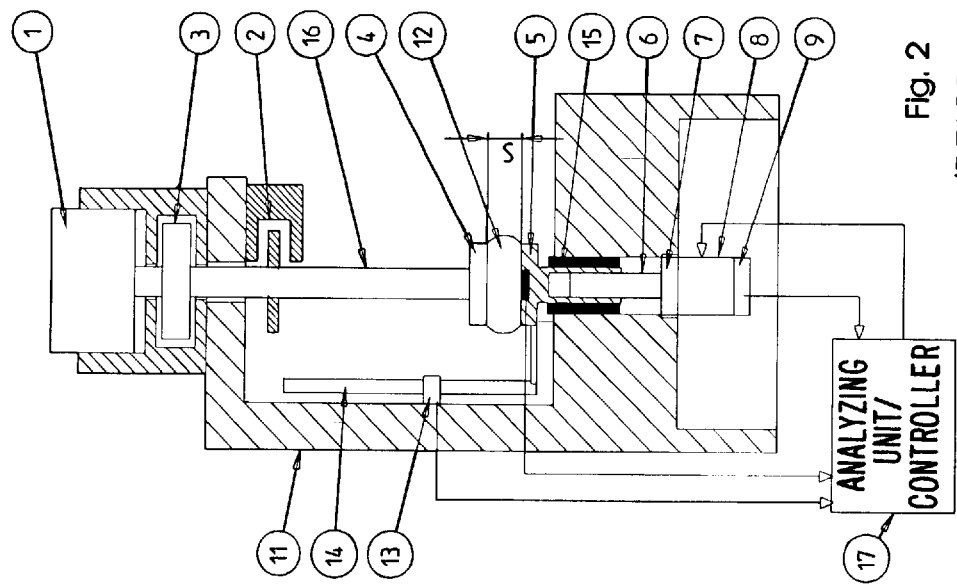
FIGS. 1 and 2 show rotational prior art rheometers.
Figure 1:
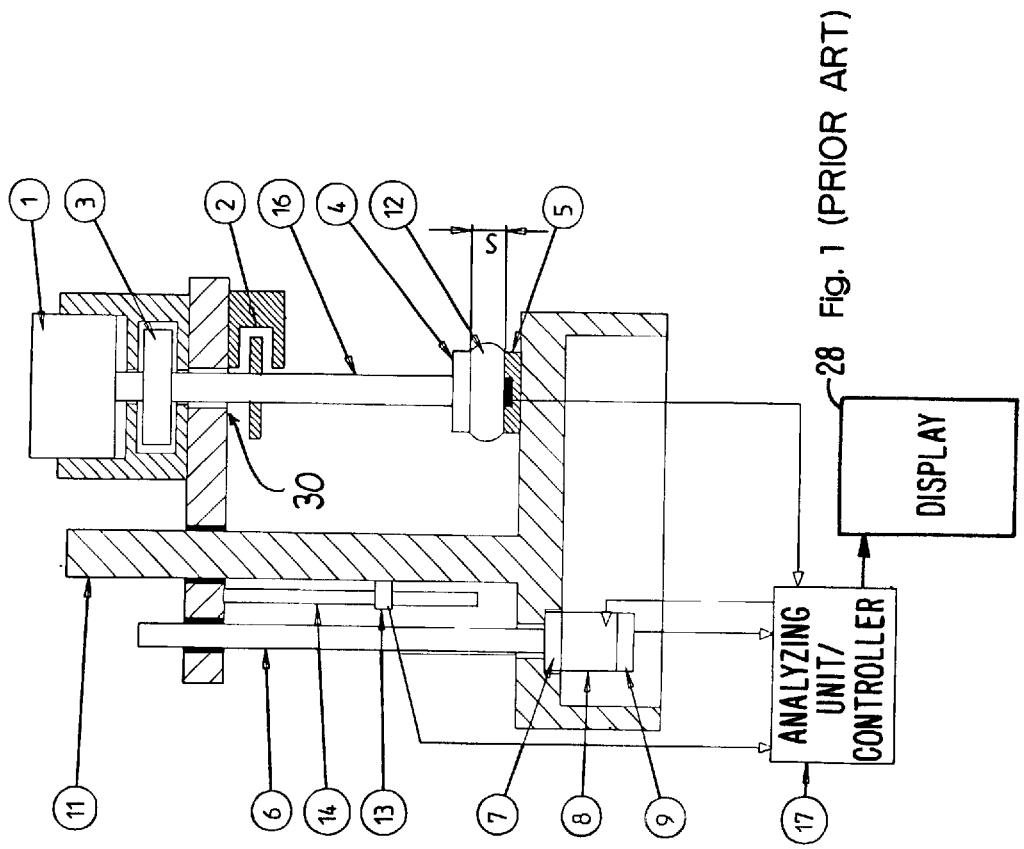

According to FIGS. 1 and 2, a rotational rheometer comprises an integrating motor 1 with the special characteristic that the torque on the motor shaft and the electricity supply, or rather the supply parameters, in particular power consumption, and/or frequency, and/or phase relationship, are in a known relationship. During a rotational test, the moment of a specimen 12 can therefore be determined by measuring the supply parameters. The relationships between the torque and the supply parameters are established by calibration.

The rotational rheometer also comprises an angle encoder 2 to determine the rotational position and rotational speed of the shaft 16. The shaft 16 is supported in a guide bearing 3. Roller bearings or air bearings are used, depending on the structure of the rotational rheometer and the torque resolution required.

Three different systems can be used for the measuring system or measuring elements 4, 5 with known geometry, namely plate/plate measuring systems as shown in FIGS. 1 to 4, cone/plate measuring systems, or cylindrical measuring systems.

The rotational rheometer also comprises a stand in the most dimensionally stable design possible.

The depth h of the measurement gap S can be set using a lifting device to adjust the height at least of one of the measuring elements 4, 5.

FIG. 1 is a diagrammatic view of a rotational rheometer where the arrangement comprising integrating motor 1, bearing system 3, angle encoder 2, and the plate-shaped measuring elements 4, 5 is connected to the stand via a linear guide 30, or is supported thereon, and is movable relative to the stand . This arrangement can be moved in a vertical direction relative to the stand 11 by means of a drive system comprising a spindle 6 with a thrust bearing 7 and a motor 8 and optionally with a flange-mounted angle encoder 9; the depth h of the measurement gap S can thus be modified thereby.

FIG. 2 shows a rotational rheometer in an arrangement modified by comparison with FIG. 1. Here the integrating motor 1, air bearing 3, and angle encoder 2 are firmly connected to the stand 11. The measurement gap S is set with an elevating platform 15, which is supported axially on the stand 11 and is driven via a spindle 6 with a thrust bearing 7 and a motor 8, which optionally has a flange-mounted angle encoder 9.

The spindle drive comprising components 6, 7, 8, and 9 can be replaced by other linear drives, e.g. an Uhing nut drive (rolling nut), linear motors, or pneumatically driven positioning devices.

There are basically three types of tests:
(a) the shaft 16 is rotated at a constant speed and the torque is measured;
(b) a constant moment is pre-selected, and the rotational speed of the shaft 16 is measured;
(c) the shaft 16 is subjected to rotary movements which are sinusoidal (or of a different waveform), a so-called oscillation test. In this type of test, both the viscous and the elastic component of the specimen 12 can be determined.

As already mentioned, the invention is explained using a plate/plate measuring system where the specimen 12 is disposed between a measuring element 5, which is in the form of a fixed plate, and a measuring element 4, which is in the form of a rotating plate. The rotating plate 4 may be of smaller dimensions than the fixed plate 5 and is usually disposed above the fixed plate 5. Measuring elements of equal size can also be used. The lower measuring element is generally a plate.

The calculated viscosity fluctuates in inverse proportion to the depth of the specimen, that is to say, a +1% measurement error produces a 1% reduction in viscosity. A measurement gap of, say, 100 μm therefore needs to be determined with an accuracy better than 1 μm.

In a cone/plate measuring system, the specimen is disposed between a fixed measuring element 5, which is in the form of a plate, and a rotating measuring element 4, which is in the form of a rotating cone with typical angles. The angles measured between the fixed plate and the cone are, for example, 0.5°, 1°, or 2°. In accordance with the specified standard, the point of the cone rests on the fixed plate. To prevent friction at this point, the point of the cone can be flattened by 50 μm and the height set so that the theoretical point of the cone again rests on the fixed plate. With cone/plate measuring systems, it is the cone geometry that determines the accuracy requirements for setting the gap. Where, for example, a 1° cone has a diameter of 25 mm, a gap error of 1.5 μm leads to a viscosity fluctuation of 1%.

The measurement gap S can be indirectly set using a linear measuring system 13, 14, as shown in FIGS. 1 and 2, with an accuracy of <1 μm. The linear measuring systems used can be sensors with resistance change (potentiometers), inductive position sensors (LVDT), or incremental position sensors, or dial gauges. Instead of position measurement, a defined measurement gap S can be set; this involves the lifting device being driven via a spindle 6 with known pitch and measuring the spindle angle (angle encoder 9), as shown in FIGS. 1 and 2. The disadvantage of this, however, is that these systems determine the distance between the lifting device and the stand and do not directly determine the height h of the measurement gap S. Under constant ambient conditions (constant room temperature, constant and equalized specimen, and measuring system temperature), measuring system gaps can therefore initially be set to the nearest micrometer, although practical experience shows that, while a specimen is undergoing Theological measurement, the measurement gap can vary by a few 0.1 mm, the reasons being as follows:

thermal expansion and mechanical deformation of the stand;
thermal expansion of the measuring element 4, the measuring element 5 and the shaft 16 (extremely severe effects are observed when temperature equalization chambers are used with a temperature range from −180° to 600° C.); and
stand rigidity and the rigidity of the shaft bearing system 3, since viscoelastic substances generate normal forces of up to some tens of newtons under shear.

High-end rheometers have a compensation device, making it possible to adjust the gap via an empirically established temperature/position function and hence to keep the gap constant. An adequate level of compensation cannot be achieved in practice, owing to the largely unknown nature of temperature equalization times, the multitude of measurement geometries, and different equalization chambers.

This is where the invention takes effect since, unlike in known rheometers, it does not establish the depth h of the measurement gap S by a circuitous route using the stand and the respective components, but, directly measures, and/or sets, and/or keeps constant the distance between the measuring elements 4, 5, i.e. a fixed plate and a rotating plate or rotating cone.

Figure 3:
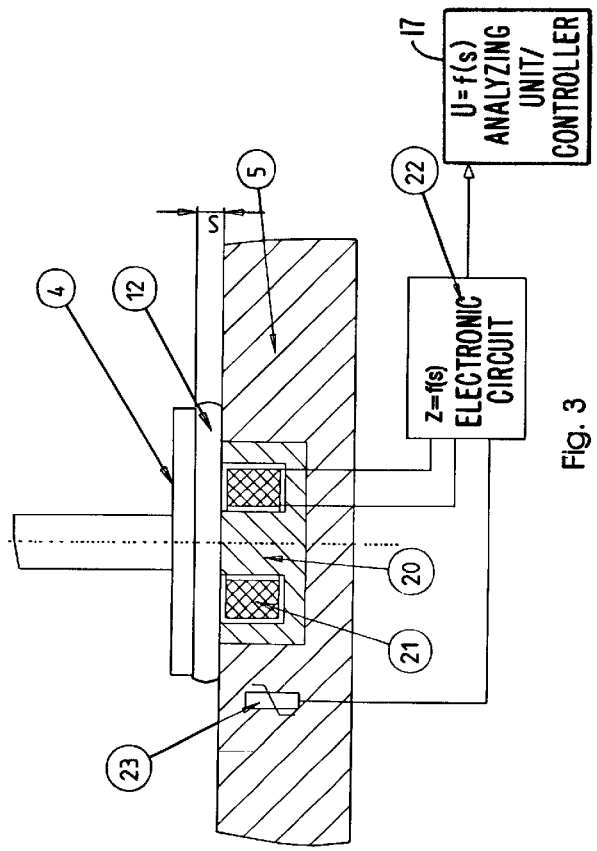

FIG. 3 is a diagrammatic view of the structure of a rotational rheometer with an inductive position sensor. The substance to be tested, or the specimen 12, is disposed in a measurement gap S between a fixed measuring element 5, which is formed by a measuring plate, and a measuring element 4, which is in the form of a plate or cone. In the fixed measuring element 5, at least one solenoid 21 is embedded in a magnetic core 20. The magnetic core may be a pot-type core, or an E-shaped or U-shaped core and is made from preferably magnetically soft material, such as soft iron, transformer sheet or ferrite. The magnetic core 20 may be made from laminated sheets, which are preferably isolated from one another, or may be made from one piece. The solenoids 21 disposed in or on the magnetic core are adapted to the shape of the magnetic core 20.

Measurement of the measurement gap S is based on the effect of the change in the electrical impedance Z of the at least one solenoid 21 in the magnetic circuit, which occurs as the measuring element 4 is brought nearer to the sensor or magnet system formed by the at least one solenoid 21 and the magnetic core 20. The depth of the measurement gap S and the impedance Z of the at least one solenoid 21 are in a fixed relationship which can be calculated or established empirically by calibration. The impedance Z and/or parts of the impedance Z of the magnet system are measured by an appropriate electrical or electronic circuit 22; from the measured values there is then obtained an output signal Z=f(S) which gives the impedance as a function of the depth of the measurement gap S. The circuit 22 therefore supplies an electric signal which is in a known function to the depth of the measurement gap S; circuit arrangements for measuring solenoid impedances are known to the person skilled in the art.

The output signals of the circuit 22 are then supplied to the analyzing unit 17 for further use, in particular to adjust the measurement gap, or keep it constant, or to analyze measurement results, or calculate required values, e.g. viscosity values. It is envisioned that, for the purpose of determining the moment of a substance to be tested 12, the relationship between the torque on the shaft of the integrating motor 1 and the supply parameters of the integrating motor 1, in particular power consumption, and/or frequency, and/or phase relationship, is known or is established by calibration, and that this relationship is advantageously stored in the analyzing unit 17.

In the embodiment of an inductive sensor described in FIG. 3, the measuring element 4 is made of a magnetically soft material and therefore forms a magnet yoke. The measuring element 4 could also support or have embedded in it a component made of magnetically soft material.

As an alternative to the position sensor described, a position sensor with an open magnetic circuit could be provided; this is known as an eddy-current sensor.

In this case (not shown), the magnetic circuit comprises a magnet core 20 and at least one solenoid 21, as described above in connection with FIG. 3. The measuring element 4 is made of material which is, in particular, a good conductor of electricity, but is not magnetic, or the element supports a component of this kind. Owing to the fact that energy is drawn from the solenoid system as a result of eddy-current losses, the bringing of the measuring element 4, or this component, closer to the magnet core 20 affects the impedance Z of the at least one solenoid 21. The depth h of the measurement gap S can again be established from the change in impedance Z.

Eddy-current sensors of this kind can also be designed without a magnetically soft core. The at least one solenoid 21 is then directly embedded in the fixed measuring element 5. The fixed measuring element 5 is made from material which is nonmagnetic and a poor conductor of electricity. The measurement gap is established or set or kept constant as described above.

According to the invention, another option is to use a magnetic position sensor. A position sensor of this kind comprises a component which is sensitive to magnetic fields, in particular a Hall-effect sensor or a magnetoresistor; these components undergo a voltage or resistance change when exposed to a magnetic field.

Figure 4:
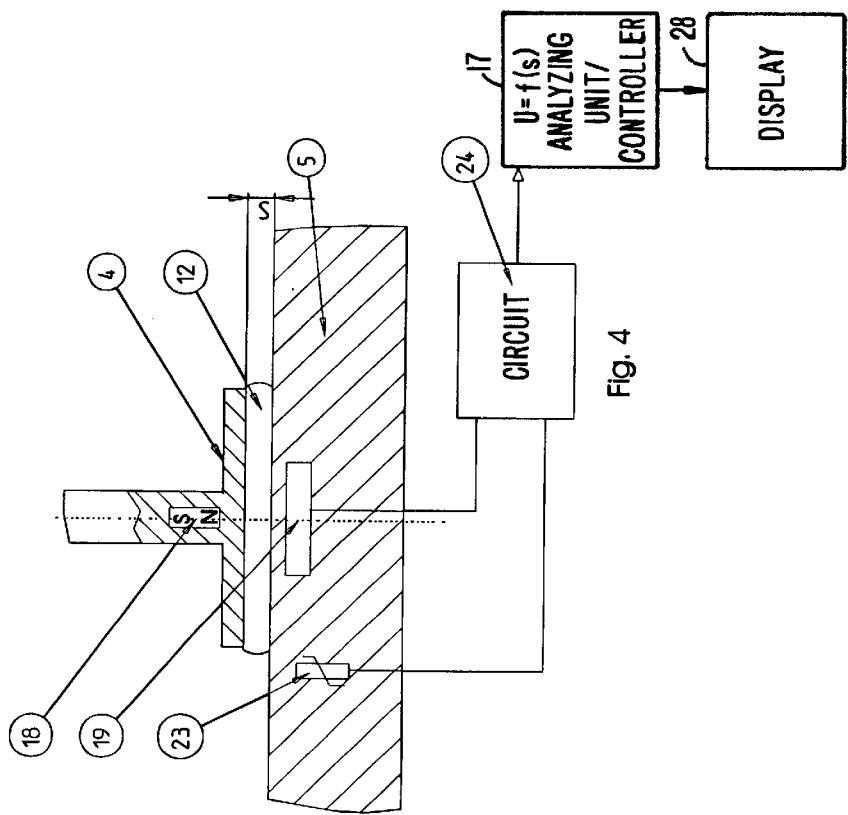
FIGS. 3 and 4 show measuring elements of rotational rheometers according to the invention with position sensors.

FIG. 4 shows an embodiment of a rheometer where there is disposed or embedded on the rotating measuring element 4 a magnetically active component, e.g. a permanent magnet 18, whose north/south polarization lies on the axis of the rotational rheometer measuring system, the polarity being irrelevant. This magnetically active component acts on the component 19 which is sensitive to magnetic fields, with the result that a fluctuation in the distance between the measuring elements 4 and 5 causes a change in the magnetic field in the region of the component 19, thereby causing in this component 19 a voltage or resistance change which is detectable in a circuit 24. The electric signal which is generated at the output of the circuit 24 and which is dependent on the depth h of the measurement gap S is supplied to the analyzing unit 17.

The measured values calculated in the analyzing unit 17 can, if necessary, appear on a visual display and/or be stored and/or be further used in an attached unit 28.

Position sensors operating on the impedance-change principle alter their impedance Z not only in dependence upon the depth h of the measurement gap S, but also with sensor temperature. The reason for this lies in the temperature-dependence of the physical properties of the materials used, e.g. permeability of the magnetically soft portions, electrical conductivity, or thermal expansion of all the sensor parts, including the measuring element 4. The temperature-dependence of the magnetically hard materials and of the magnetic field sensors also has to be allowed for with magnetic position sensors.

Temperature is measured with a temperature sensor 23, which is located in the position sensor 19, 21 or as close as possible to the position sensor 19, 21. The temperature measurement is supplied to the circuit 22 or 24 or the downstream analyzing unit 17; as a result, the effect of temperature on the size of the measurement gap S can be largely compensated for. The temperature-dependence of the position sensor is established empirically in a reference operation covering temperature within the application range at various constant gap sizes.

The measurement results can be analyzed and/or the depth of the measurement gap S can be set in various ways, as follows.

(a) Position Sensor with Absolute Measurement:

A calibration procedure enables a position sensor of the design described above to be adjusted to an absolute linear scale (e.g. millimeters). The disadvantage is that a separate calibration procedure has to be carried out for all measuring elements with different geometries.

The required measurement gap S is set using the lifting device and the control electronics 17, the true value being supplied by the position sensor.

One possibility is to keep the measurement gap constant for the duration of a Theological measurement; this involves the control electronics continuously comparing the true value with the setpoint value and keeping the measurement gap S constant by re-adjustment using the lifting device. The other possibility is to allow for the true value of the measurement gap when calculating the rheological variables. Both procedures compensate for the effect of the gap change on the Theological measurement results.

(b) Position Sensor with Relative Measurement:

To set the gap, the rheometer controller 17 establishes the gap zero point by, for example, bringing the measuring element 4 towards the fixed measuring element 5 with the lifting device until the measuring elements meet. The increase in torque caused by contact friction is used as recognition of this.

Another procedure for recognizing the gap zero point is based on the sudden increase in force in the axial direction of the measuring system when the two elements meet. This force can be detected with a normal force measuring device provided on the rheometer. Other methods are quite conceivable, including, for example, a detectable current short when the two measuring elements 4 and 5 come into contact. This lifting device position value is stored as the zero position. The procedure is then as follows:

the gap is opened to a few millimeters and the specimen introduced;

the measuring element 4 is lowered to set the pre-selected gap depth. The depth is set using the rheometer's lifting measurement device;

the signal value (gap reference value) supplied by the position sensor is stored, and rheological measurement begins;

the true signal value supplied by the position sensor is continuously compared with the gap reference value (setpoint value) by the rheometer controller 17. In the event of a deviation from the norm, the gap is re-adjusted using the lifting device and thus kept constant.

The relative measurement method described is less complicated than calibrating the rheometer to an absolute distance scale, which would have to be repeated or recalibrated each time a sensor or measuring element was replaced.

What is claimed is:

1. A rotational rheometer with an integrating motor, which rotates a measuring shaft supporting a first measuring element, there being formed between this first measuring element and a second, fixed measuring element, a measurement gap, into which is introduced the substance to be tested, the depth of the measurement gap being variable by the adjustment of the first and second measuring elements relative to each other, and a device being provided to determine a mutual distance between the first and second measuring elements, wherein in order to establish or measure, and/or set, and/or keep constant the depth of the measurement gap in a non-contact manner, at least one inductive or at least one magnetic position sensor generates output signals and is supported by one of the first and second measuring elements;

the first measuring element causes the position sensor disposed on the second measuring element to respond in dependence upon the distance between the first and second measuring elements or causes an output signal of the at least one position sensor to be modified; and the output signals of the at least one position sensor are supplied to an analyzing unit.

2. A rotational rheometer according to claim 1, wherein the position sensor supported by the second measuring element comprises an inductive position sensor having at least one solenoid supported by the second measuring element or embedded in the second measuring element, the first measuring element supporting a component made of magnetically soft material, or the first measuring element being made of magnetically soft material at least in a region facing the solenoid, and the impedance values of the at least one solenoid being supplied to the analyzing unit as output signals of the inductive position sensor.

3. A rotational rheometer according to claim 2, wherein the at least one solenoid carries one of alternating current and alternating voltage.

4. A rotational rheometer according to claim 2, wherein the at least one solenoid comprises a solenoid core.

5. A rotational rheometer according to claim 2, wherein the at least one solenoid is partly embedded in the second measuring element.

6. A rotational rheometer according to claim 2, wherein the component or the first measuring element being made of magnetically soft material faces the solenoid in its entirety.

7. A rotational rheometer according to claim 1, wherein the position sensor supported by the second measuring element comprises an inductive position sensor with at least one solenoid supported by the second measuring element or embedded in this measuring element, the first measuring element supporting at least one component made of electrically conductive, nonmagnetic material, or the first measuring element being made of electrically conductive, nonmagnetic material at least in a region facing the solenoid, and the impedance values of the at least one solenoid being supplied to the analyzing unit as output signals of the inductive position sensor.

8. A rotational rheometer according to claim 7, wherein the second measuring element is made from material which is nonmagnetic and a poor conductor of electricity, and wherein the solenoid supported by the second measuring element is formed without a core.

9. A rotational rheometer according to claim 7, wherein the impedance values of the at least one solenoid can be modified by eddy-current losses.

10. A rotational rheometer according to claim 1, wherein the position sensor supported by the second measuring element is a component which responds to magnetic fields;

a permanent magnet is supported by the first measuring element or is embedded in the first measuring element, an axis of the permanent magnet preferably being aligned perpendicularly to a face of the position-sensor or to a surface of the second measuring element supporting the magnetic position sensor; and characteristics of the component which can be influenced by magnetic fields are supplied to the analyzing unit.

11. A rotational rheometer according to claim 10, wherein the component is one of a Hall-effect sensor and a magnetoresistor.

12. A rotational rheometer according to claim 10, wherein the characteristics of the component which can be influenced by magnetic fields comprises one of voltage values and resistance values.

13. A rotational rheometer according to claim 1, wherein, for the purpose of measuring the temperature of at least one of the position sensors, the measuring elements, and their surrounding areas, there is provided a temperature sensor associated with the position sensor, output signals of the temperature sensor being supplied to the analyzing unit for temperature compensation of the output signals of the position sensor.

14. A rotational rheometer according to claim 13, wherein the temperature sensor is supported by one of the measuring elements.

15. A rotational rheometer according to claim 1, wherein the first and second measuring elements are disposed one above the other, and the position sensor is disposed on a lower one of the measuring elements.

16. A rotational rheometer according to claim 15, wherein the lower one of the measuring elements is of a size equal to or larger than another one of the measuring elements.

17. A rotational rheometer according to claim 1, wherein, for the purpose of setting the distance between the first and second measuring elements, there are provided devices for moving the measuring elements relative to each other, said devices being formed by at least one of linear drives, spindle drives, and Uhing nut drives.

18. A rotational rheometer according to claim 1, wherein the second measuring element comprises at least one solenoid set in or on a U-shaped or E-shaped core made of soft iron, transformer sheet, or ferrite.

19. A rotational rheometer according to claim 1, wherein the second measuring element comprises at least one solenoid or a component which responds to magnetic fields, and wherein, in order to calculate or establish the impedance of the solenoid, or the voltage, or resistance value of a component, a computer is operatively coupled to the analyzing unit.

20. A rotational rheometer according to claim 19, wherein the computer is adapted to adjust the calculated or established impedance of the solenoid as a function of temperature values determined by a temperature sensor.

21. A rotational rheometer according to claim 1, wherein the analyzing unit generates further signals in dependence upon the output signals of the position sensor for controlling a device for modifying the measurement gap by adjusting the height at least of one of the first and second measuring elements.

22. A rotational rheometer according to claim 1, wherein the first measuring element comprises a member disposed on the second measuring element.

* * * * *